United States Patent
Okoniewski et al.

(10) Patent No.: US 10,166,376 B2
(45) Date of Patent: Jan. 1, 2019

(54) RESTRICTED EXPANSION DISSECTOR

(71) Applicant: Covidien LP, Mansfield, MA (US)

(72) Inventors: Greg Okoniewski, North Haven, CT (US); Jay Breindel, Kensington, CT (US); Elias Hartoumbekis, New Haven, CT (US)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 14/247,286

(22) Filed: Apr. 8, 2014

(65) Prior Publication Data
US 2014/0364892 A1    Dec. 11, 2014

Related U.S. Application Data

(60) Provisional application No. 61/833,610, filed on Jun. 11, 2013.

(51) Int. Cl.
*A61B 17/32*    (2006.01)
*A61M 29/00*    (2006.01)
(Continued)

(52) U.S. Cl.
CPC ......... *A61M 29/00* (2013.01); *A61B 17/0218* (2013.01); *A61B 17/32* (2013.01);
(Continued)

(58) Field of Classification Search
CPC ...... A61B 17/2018; A61B 2017/00557; A61B 2017/00831; A61B 2017/00907; A61B 2017/0225; A61B 2017/320048; A61B 2090/064; A61B 17/32; A61B 17/02; A61M 29/00; A61M 25/10–25/104
(Continued)

(56) References Cited

U.S. PATENT DOCUMENTS 397,060 A    1/1889    Knapp
512,456 A    9/1894    Sadikova
(Continued)

FOREIGN PATENT DOCUMENTS

CN    1622792 A    6/2005
CN    101461981 A    6/2009
(Continued)

OTHER PUBLICATIONS

European Examination Report dated Oct. 14, 2015, issued in European Application No. 14171723.
(Continued)

*Primary Examiner* — Eric J Rosen
*Assistant Examiner* — George J Ulsh (57) ABSTRACT

A surgical apparatus is disclosed that is configured and dimensioned to create an internal surgical worksite. The surgical apparatus includes a dissection element that is repositionable between an unexpanded condition, wherein the dissection element defines a first outer transverse cross-sectional dimension, and an expanded condition, wherein the dissection element defines a second, larger outer transverse cross-sectional dimension. The surgical apparatus further includes a restrictor that is in contact with the dissection element in order to restrict expansion of the dissection element in at least one direction.

15 Claims, 7 Drawing Sheets

(51) Int. Cl.
*A61B 17/02* (2006.01)
*A61B 17/00* (2006.01)
*A61B 90/00* (2016.01)

(52) U.S. Cl.
CPC .............. *A61B 2017/00557* (2013.01); *A61B 2017/00831* (2013.01); *A61B 2017/00907* (2013.01); *A61B 2017/0225* (2013.01); *A61B 2017/320048* (2013.01); *A61B 2090/064* (2016.02)

(58) Field of Classification Search
USPC ....................................................... 606/191
See application file for complete search history.

(56) References Cited

U.S. PATENT DOCUMENTS

| | | |
|---|---|---|
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,479,497 A | 10/1984 | Fogarty et al. |
| 4,490,137 A | 12/1984 | Moukheibir |
| 4,496,345 A | 1/1985 | Hasson |
| 4,526,175 A | 7/1985 | Chin et al. |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,706,670 A | 11/1987 | Andersen et al. |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A * | 6/1992 | Allgood ................ A61B 17/34 604/105 |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,429 A * | 7/1994 | Noguchi ........... A61M 25/1027 604/103.09 |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,480 A | 9/1997 | Knight et al. |
| 5,667,520 A | 9/1997 | Bonutti |
| 5,690,668 A | 11/1997 | Fogarty et al. |
| 5,695,514 A | 12/1997 | Chin |
| 5,702,416 A | 12/1997 | Kieturakis et al. |
| 5,704,372 A | 1/1998 | Moll et al. |
| 5,707,382 A | 1/1998 | Sierocuk et al. |
| 5,713,869 A | 2/1998 | Morejon |
| 5,722,934 A | 3/1998 | Knight et al. |
| 5,722,986 A | 3/1998 | Smith et al. |
| 5,728,119 A | 3/1998 | Smith et al. |
| 5,730,748 A | 3/1998 | Fogarty et al. |

(56) References Cited

U.S. PATENT DOCUMENTS

| | | | |
|---|---|---|---|
| 5,730,756 | A | 3/1998 | Kieturakis et al. |
| 5,738,628 | A | 4/1998 | Sierocuk et al. |
| 5,755,693 | A | 5/1998 | Walker et al. |
| 5,762,604 | A | 6/1998 | Kieturakis |
| 5,772,680 | A | 6/1998 | Kieturakis et al. |
| 5,779,728 | A | 7/1998 | Lunsford et al. |
| 5,797,947 | A | 8/1998 | Mollenauer |
| 5,814,059 | A | 9/1998 | Hart et al. |
| 5,814,060 | A | 9/1998 | Fogarty et al. |
| 5,836,871 | A | 11/1998 | Wallace et al. |
| 5,836,913 | A | 11/1998 | Orth et al. |
| 5,836,961 | A | 11/1998 | Kieturakis et al. |
| RE36,043 | E | 1/1999 | Knighton |
| 5,865,728 | A | 2/1999 | Moll et al. |
| 5,865,802 | A | 2/1999 | Yoon et al. |
| 5,873,889 | A | 2/1999 | Chin |
| 5,893,866 | A | 4/1999 | Hermann et al. |
| 5,902,316 | A | 5/1999 | Mollenauer |
| 5,904,699 | A | 5/1999 | Schwemberger et al. |
| 5,925,058 | A | 7/1999 | Smith et al. |
| 5,968,066 | A | 10/1999 | Fogarty et al. |
| 6,013,090 | A | 1/2000 | Fogarty et al. |
| 6,036,714 | A | 3/2000 | Chin |
| 6,102,928 | A | 8/2000 | Bonutti |
| 6,152,895 | A | 11/2000 | Wilk |
| 6,168,608 | B1 | 1/2001 | Echeverry et al. |
| 6,312,442 | B1 | 11/2001 | Kieturakis et al. |
| 6,361,543 | B1 | 3/2002 | Chin et al. |
| 6,368,337 | B1 | 4/2002 | Kieturakis et al. |
| 6,432,121 | B1 | 8/2002 | Jervis |
| 7,300,448 | B2 | 11/2007 | Criscuolo et al. |
| 7,744,617 | B2 | 6/2010 | Lunsford et al. |
| 8,500,770 | B2 | 8/2013 | Echevery et al. |
| 8,540,745 | B2 | 9/2013 | Criscuolo et al. |
| 2003/0004529 | A1 | 1/2003 | Tsonton et al. |
| 2003/0040789 | A1* | 2/2003 | Colgan ............... A61F 2/90 623/1.11 |
| 2007/0108845 | A1 | 5/2007 | Crane |
| 2009/0182368 | A1 | 7/2009 | Lunsford et al. |
| 2009/0275972 | A1* | 11/2009 | Uemura ............. A61B 17/0401 606/192 |
| 2012/0083797 | A1* | 4/2012 | Cabrera ........... A61B 17/00234 606/114 |
| 2012/0203220 | A1 | 8/2012 | Brannan et al. |
| 2012/0303018 | A1 | 11/2012 | Ladtkow et al. |
| 2014/0276406 | A1* | 9/2014 | Campbell ........... A61M 25/104 604/103.02 |

FOREIGN PATENT DOCUMENTS

| | | |
|---|---|---|
| EP | 480653 A1 | 4/1992 |
| EP | 0610099 A2 | 8/1994 |
| EP | 1913903 A2 | 4/2008 |
| JP | 41444572 | 5/1992 |
| WO | 8200408 A1 | 2/1982 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9324172 A1 | 12/1993 |
| WO | 9912602 A1 | 3/1999 |
| WO | 0296307 A2 | 12/2002 |
| WO | 2012129054 A1 | 9/2012 |

OTHER PUBLICATIONS

European Search Report dated Nov. 21, 2014 issued in European Application No. 14 17 1723.
Chinese Office Action dated Aug. 17, 2017, issued in Chinese Application No. 2014102319755.

* cited by examiner

RESTRICTED EXPANSION DISSECTOR

CROSS-REFERENCE TO RELATED APPLICATIONS

This application claims the benefit of, and priority to, U.S. Provisional Patent Application Ser. No. 61/833,610, filed Jun. 11, 2013, which is hereby incorporated by reference.

TECHNICAL FIELD

The present disclosure generally relates to an apparatus and method for creating a surgical worksite inside a patient's body through an opening in tissue. More specifically, the present disclosure relates to a surgical apparatus that includes an expandable dissection element for separating adjacent tissue layers, and corresponding methods of use.

BACKGROUND

During certain surgical procedures, it may become necessary to separate adjacent tissue layers in order to create an internal surgical worksite. Various dissectors useful in the formation of such worksites are known, and typically include an expandable dissection element, e.g., a balloon, that is supported on the distal end of a tube. A need remains, however, for increased control over the expansion of such dissection elements in order to selectively limit tissue displacement during formation of the surgical worksite. The present disclosure addresses this need, among others, and describes a surgical apparatus including an expandable dissection element that allows for an increased level of control over expansion of the dissection element in one or more directions.

SUMMARY

In one aspect of the present disclosure, a surgical apparatus is disclosed that is configured and dimensioned to create an internal surgical worksite. The surgical apparatus includes a dissection element, and a restrictor that is in contact with the dissection element.

The dissection element is repositionable between an unexpanded condition, wherein the dissection element defines a first outer transverse cross-sectional dimension, and an expanded condition, wherein the dissection element defines a second, larger outer transverse cross-sectional dimension. The restrictor element is configured and dimensioned to restrict expansion of the dissection element in at least one direction.

The dissection element may be at least partially formed from a material permitting at least some light to pass therethrough. For example, the dissection element may include translucent portions, transparent portions, opaque portions, or combinations thereof.

The restrictor may be configured to restrict expansion of the dissection element such that the dissection element defines a generally planar configuration in the expanded condition, according to the definition provided herein.

The dissection element and the restrictor may have different resiliencies.

The dissection element may be at least partially formed from a first material, and the restrictor may be at least partially formed from a second material different than the first material. For example, the dissection element may be at least partially formed from a material having a first durometer, and the restrictor may be at least partially formed from a material having a second, greater durometer.

The dissection element may be at least partially formed from urethane, and the restrictor may be at least partially formed from ripstop nylon.

The dissection element and the restrictor may be configured as discrete structures.

The restrictor may be positioned externally of the dissection element. Alternatively, the restrictor may be positioned internally within the dissection element, or between adjacent layers of the material(s) from which the dissection element is formed.

The restrictor may include a pair of first arms and a pair of second arms, wherein the pair of first arms are secured together, and the pair of second arms are secured together. For example, the pair of first arms may be welded together, and the pair of second arms may be welded together.

The pair of first arms and the pair of second arms may also be secured to the material from which the dissection element is formed.

The restrictor may define a contour corresponding to that defined by the dissection element in the expanded condition. For example, the arms of the restrictor may include portions that are curvate in configuration.

The dissection element and the restrictor may be at least partially formed from the same material, e.g., urethane, and may be integrally formed. In such embodiments, the dissection element may define a first thickness, and the restrictor element may define a second, greater thickness.

In another aspect of the present disclosure, a restrictor is disclosed that is configured for use with an expandable dissection element during the creation of an internal surgical worksite. The restrictor includes a first portion including first and second arms, and a second portion connected to the first portion that also includes first and second arms. The first arm of the first portion is secured to the first arm of the second portion, and the second arm of the first portion is secured to the second arm of the second portion such that the restrictor restricts expansion of the dissection element in at least one direction.

The restrictor may be configured and dimensioned to restrict expansion of the dissection element such that the dissection element defines a generally planar configuration in the expanded condition.

The first arm of the first portion may be welded to the first arm of the second portion, and the second arm of the first portion may be welded to the second arm of the second portion.

The first and second arms of the first portion, and the first and second arms of the second portion, may be secured to the material from which the dissection element is formed.

The restrictor may define a contour corresponding to that defined by the dissection element upon expansion. For example, the arms of the restrictor may include portions that are curvate in configuration.

The restrictor may be at least partially formed from a material less resilient than that included in the dissection element, e.g., the material from which the dissection element is formed.

The restrictor may be positioned externally of the dissection element. Alternatively, the restrictor may be positioned internally within the dissection element, or between adjacent layers of the material(s) from which the dissection element is formed.

The materials of construction used in formation of the restrictor and the dissection element may be different. For example, the restrictor may be at least partially formed from a material having a higher durometer than that included in the dissection element, e.g., the material from which the dissection element is formed.

The restrictor may be at least partially formed from ripstop nylon.

The restrictor may be at least partially formed from a material permitting at least some light to pass therethrough.

In yet another aspect of the present disclosure, a method of performing a surgical procedure is disclosed that includes inserting a surgical apparatus into an opening in tissue, expanding a dissection element of the surgical apparatus to separate adjacent layers of the tissue to form an internal surgical worksite, and mechanically restricting expansion of the dissection element in at least one direction via a restrictor in contact with the dissection element subjecting the dissection element to an inwardly directed force.

Expanding the dissection element may include communicating fluid into the dissection element, e.g., through a cannula assembly supporting the dissection element.

Mechanically restricting expansion of the dissection element may include limiting the dissection element to a generally planar configuration upon expansion.

The disclosed method may further include visualizing the internal surgical worksite through the dissection element. For example, visualizing the internal surgical worksite may include passing a visualization instrument into the dissection element, e.g., through a cannula assembly supporting the dissection element.

In another aspect of the present disclosure, a surgical apparatus is disclosed that is configured and dimensioned to create an internal surgical worksite. The surgical apparatus includes a dissection element that is repositionable between an unexpanded condition, wherein the dissection element defines a first outer transverse cross-sectional dimension, and an expanded condition, wherein the dissection element defines a second, larger outer transverse cross-sectional dimension.

The dissection element may be at least partially formed from one or more layers of material restricting expansion of the dissection element in one or more dimensions beyond a predetermined measure. For example, the one or more layers of material may restrict expansion of the dissection element beyond a particular volume, or may restrict expansion of the dissection element such that the expansion element defines a particular configuration in the expanded condition.

The dissection element may be formed from a single material, e.g., ripstop nylon. Alternatively, the dissection element may be at least partially formed from one or more layers of film having a high modulus of elasticity, e.g., high durometer polyurethane, polyethylene, or mylar.

Alternatively, the dissection element may be formed from a layer of first material that is reinforced with a second, different material, e.g., a layer of urethane film that is reinforced with ripstop nylon or flashspun high-density polyethylene fibers.

Alternatively, the dissection element may be formed from a first layer of material that is secured to a second layer of material at one or more junction points that restrict expansion of the dissection element in directions transverse, e.g., perpendicular, to the one or more junction points.

DETAILED DESCRIPTION

Embodiments of the present disclosure will now be described in detail with reference to the drawings, wherein like reference numerals identify similar or identical elements. As used herein, the term "patient" refers to a human or animal patient, and the term "clinician" refers to a doctor, nurse, support personnel, or other care provider. While the devices, systems, and methodologies described herein are discussed and illustrated in the context of an abdominal procedure, the principles of the present disclosure are equally applicable to other surgical procedures performed in alternate locations within a patient's body, e.g., vascular procedures, cardiac procedures, and urinary procedures.

Figure 1:
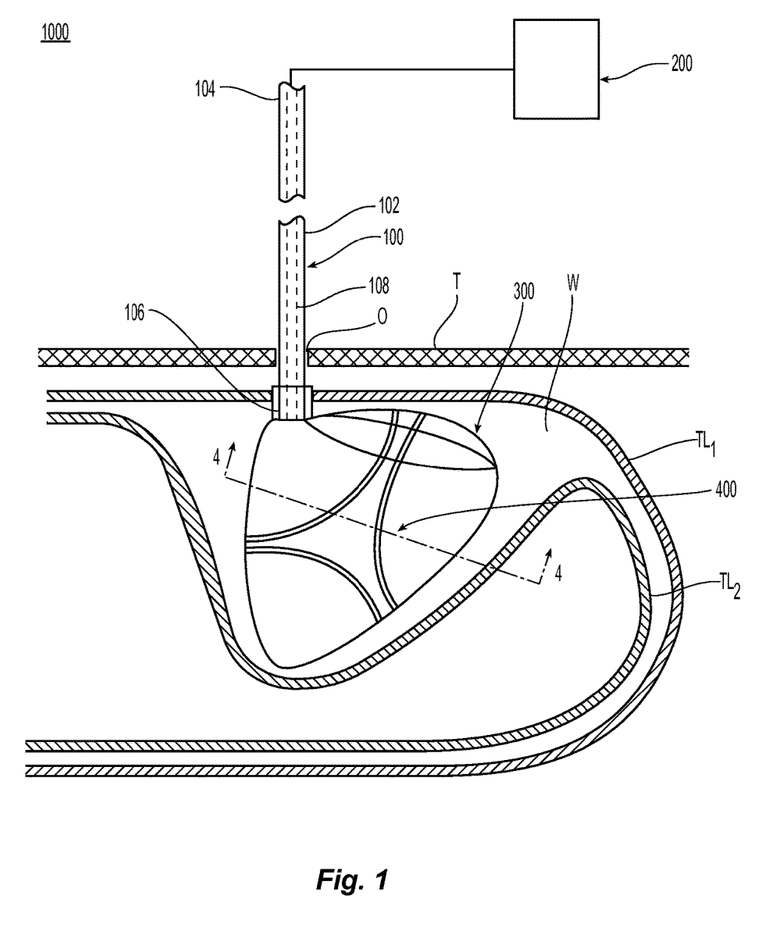
FIG. 1 is a partial cross-sectional illustration showing the use of a dissector assembly including an expandable dissection element and a restrictor in accordance with one embodiment of the present disclosure to create an internal worksite during a surgical procedure.
Figure 2:
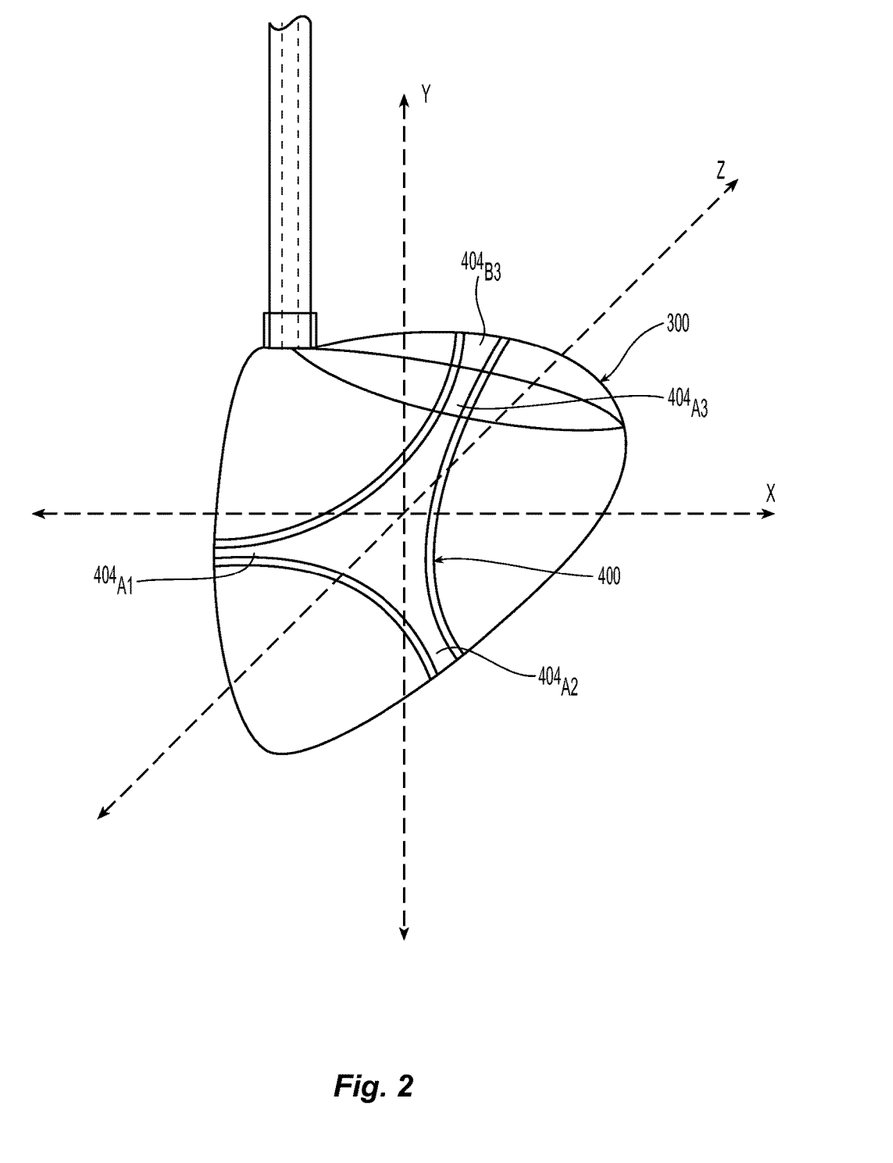
FIG. 2 illustrates the dissector assembly seen in FIG. 1 removed from the internal worksite.

FIGS. 1 and 2 illustrate a dissector assembly 1000 in accordance with the principles of the present disclosure that includes a cannula assembly 100, shown in communication with a fluid source 200, and an expandable dissection element 300, e.g., a balloon, bladder, or the like, that is supported by the cannula assembly 100. The dissector assembly 1000 is configured and dimensioned to create, and facilitate access to, an internal worksite W within a patient. For example, the dissector assembly 1000 may be utilized beneath a patient's external tissue T to form the internal worksite W between adjacent tissue layers $TL_1$, $TL_2$.

The cannula assembly 100 includes a shaft 102 having a proximal end 104 that is in communication with the fluid source 200, and a distal end 106 that supports the dissection element 300. The shaft 102 includes a lumen 108 extending therethrough that facilitates the communication of fluid, e.g., a liquid, a gas, or a combination thereof, from the fluid source 200 into the dissection element 300 to permit expansion thereof. To regulate the flow of fluid from the fluid source 200 to the dissection element 300, the cannula assembly 100 may include one or more valves (not shown).

The dissection element 300 is repositionable from an initial, unexpanded condition to an expanded condition via the communication of fluid into the dissection element 300, during which time, the dissection element 300 is enlarged in three dimensions, i.e., along the X, Y, and Z axes (FIG. 2). In the unexpanded condition, the dissection element 300 defines a first outer transverse cross-sectional dimension, and in the expanded condition, (FIGS. 1 and 2), the dissection element 300 is enlarged to define a second outer transverse cross-sectional dimension larger than the first outer transverse cross-sectional dimension. For example, in moving from the unexpanded condition to the expanded condition, the dimensions of the dissection element 300 may be increased along one or more of the X, Y, and Z axes (FIG. 2).

Figure 3:
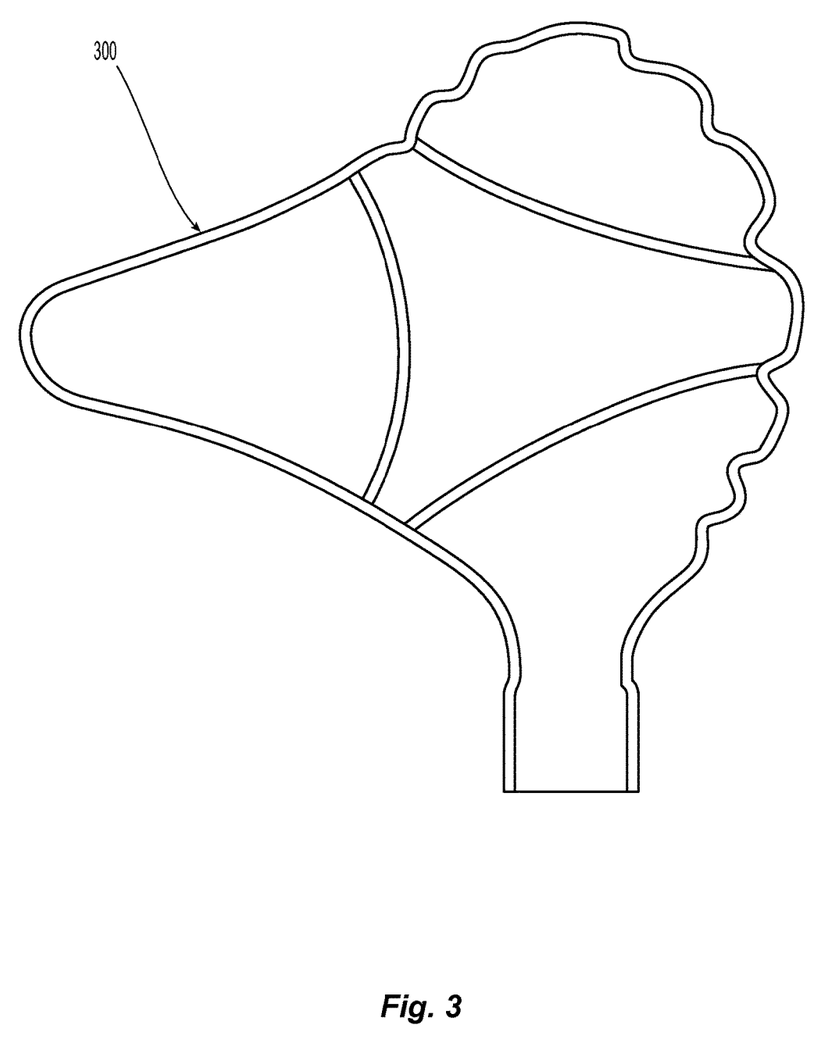
FIG. 3 illustrates an alternate embodiment of the presently disclosed dissector assembly.

In addition to the configurations seen in FIGS. 1 and 2, the dissection element 300 may be configured to achieve any desired shape in the expanded condition, dependent upon the particular requirements of the surgical procedure in which the dissector assembly 1000 is employed. For example, in the expanded condition, the dissection element 300 may be configured as illustrated in FIG. 3, or alternatively, the dissection element 300 may define a circular configuration, an oval configuration, a kidney-shaped configuration, a triangular configuration, a toroidal configuration, etc. The dissection element 300 may be formed from any material of construction suitable for the intended purpose of permitting expansion of the dissection element 300 in the manner described herein.

In one embodiment of the disclosure, in order to facilitate visualization through the dissection element 300, e.g., during the separation of tissue and formation of the internal worksite W (FIG. 1), the dissection element 300 may be formed, either in whole or in part, from a material permitting at least some light to pass therethrough, e.g., clear urethane. For example, the dissection element 300 may include translucent portions, transparent portions, or combinations thereof, as well as opaque portions.

Figure 4:
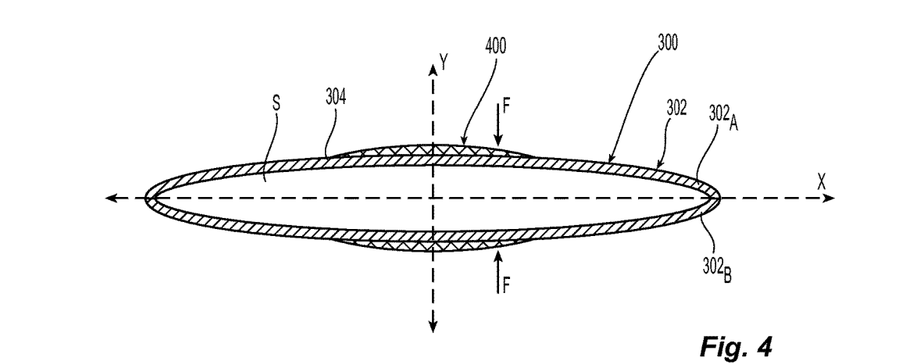
FIG. 4 is a cross-sectional illustration of the dissection element and the restrictor seen in FIG. 1 along line 4-4.

With reference now to FIG. 4, in one embodiment, the dissection element 300 includes, e.g., is formed from, one or more layers 302 of material that are secured together to define an interior space S. For example, in the embodiment illustrated in FIG. 4, the dissection element 300 is formed by securing together two layers $302_A$, $302_B$ of material at the perimeters thereof, or any other suitable location. The layers $302_A$, $302_B$ of material may be secured together through any suitable manufacturing procedure, including, but not limited to, welding via impulse, laser, or RF, or through the use of an adhesive. Alternatively, the layers 302 may be formed monolithically, either partially or entirely.

Figure 5:
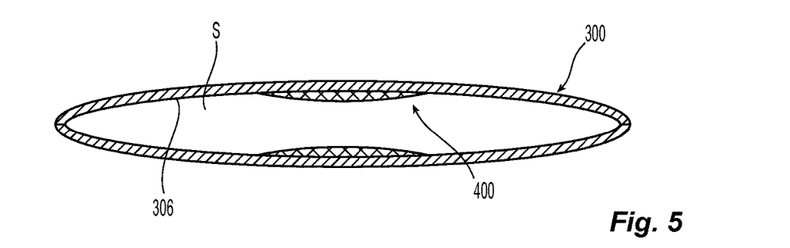
FIGS. 5 and 6 are cross-sectional illustrations of alternate embodiments of the presently disclosed dissection element and restrictor.
Figure 6:
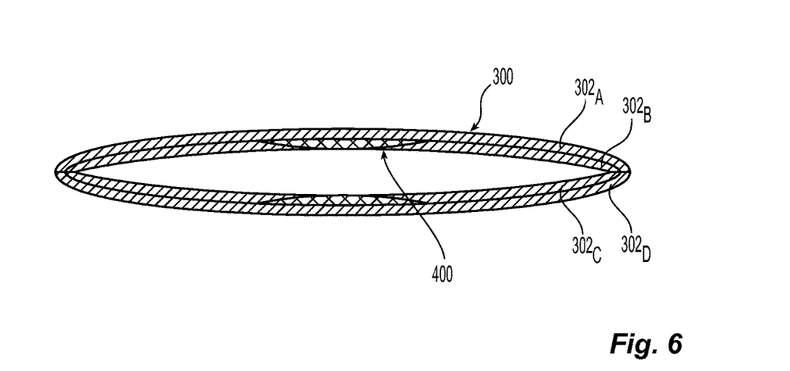

In order to restrict expansion of the dissection element 300, and achieve a desired configuration in the expanded condition, the dissector assembly 1000 further includes a restrictor 400 (FIGS. 1, 2, 4, and 7). In the embodiment of the disclosure illustrated in FIGS. 1, 2, 4, and 7, the restrictor 400 is provided as an additional, discrete component of the dissector assembly 1000 that is in contact with, e.g., secured to, the dissection element 300. For example, the restrictor 400 may be secured to an outer surface 304 of the dissection element 300, either fixedly or removably, so as to at least partially envelop the dissection element 300, as seen in FIGS. 1, 2, and 4. Alternatively, as seen in FIG. 5, the restrictor 400 may be secured to an internal surface 306 of the dissection element 300 such that the restrictor 400 is positioned within the interior space S. In another embodiment of the disclosure, which is illustrated in FIG. 6, it is envisioned that the restrictor element 400 may be embedded between adjacent layers $302_A$, $302_B$ and between adjacent layers $302_C$, $302_D$ of the material from which the dissection element 300 is formed. Alternatively, the restrictor 400 may be monolithically formed with at least one of the layers 302 of the dissection element 300.

The restrictor 400 may entirely prevent expansion of one or more portions of the dissection element 300 in one or more directions. It is also contemplated, however, that the restrictor 400 may simply limit expansion of one or more portions of the dissection element 300, and permit a certain degree of expansion of the one or more portions.

The resiliency of the restrictor 400 may be less than that of the dissection element 300. For example, the dissection element 300 may be at least partially formed from a first material having a first durometer, e.g., clear urethane, and the restrictor 400 may be at least partially formed from a second, different material having a second, higher durometer, and/or increased rigidity, and/or decreased flexibility, e.g., ripstop nylon, a metallic alloy, a textile, or combinations thereof. Alternatively, it is contemplated that portions of the restrictor 400 may include the same material as the dissection element 300.

The reduced resiliency of the restrictor 400 compared to that of the dissection element 300 may be accomplished in various ways. For example, the restrictor 400 may include more layers 302 of material than the dissection element 300, or the restrictor 400 may be of a greater thickness than the dissection element 300. Additionally, or alternatively, the restrictor 400 may include a substantially rigid material, or may define a perimeter having lesser flexibility than the remainder of the restrictor 400.

The reduced resiliency of the restrictor 400 compared to that of the dissection element 300 allows the restrictor 400 to selectively inhibit expansion of the dissection element 300 along one or more of the axes X, Y, Z (FIG. 2), dependent upon the particular configuration of the restrictor 400, and the orientation of the restrictor 400 in relation to the dissection element 300. As seen in FIG. 4, for example, the restrictor 400 may be configured, dimensioned, and positioned to restrict expansion of the dissection element 300 along the Y axis in order to prevent the dissection element 300 from assuming a spherical configuration, and instead, realize a flattened, oblong, or otherwise generally planar configuration in the expanded condition. Throughout the present disclosure, the term "generally planar" is used to describe the configuration of the dissection element 300 in the expanded condition, in which the dissection element 300 may not be perfectly planar in configuration, and may include both curvilinear portions and straight portions. For example, dependent upon the particular configuration of the restrictor 400, the portions of the dissection element 300 immediately adjacent to, or in contact with, the restrictor 400 may be either flat, or may include a slight curvature, e.g., less than 20°, whereas those portions of the dissection element 300 further from the restrictor 400 may include a greater curvature. In the context of the particular embodiment show in FIG. 4, the portions of the dissection element 300 immediately adjacent to the restrictor 400 are generally flat, with a relatively constant dimension along the Y axis, in contrast to those portions of the dissection element 300 spaced outwardly from the restrictor 400, i.e., along the X axis, which include a more variable dimension along the Y axis.

In one embodiment, the restrictor 400 defines a contour corresponding to that defined by the outer surface 304 (FIG. 4) of the dissection element 300. For example, with reference to FIG. 7, which illustrates the restrictor 400 separated from the dissection element 300, the restrictor 400 may include first and second portions $402_A$, $402_B$, respectively, wherein the first portion $402_A$ includes a first arm $404_{A1}$, a second arm $404_{A2}$, and a third arm $404_{A3}$, and the second portion $402_B$ includes a first arm $404_{B1}$, a second arm $404_{B2}$, and a third arm $404_{B3}$. In order to mimic the contour defined by the dissection element 300 in the expanded condition, each of the arms $404_{A1}$, $404_{A2}$, and $404_{A3}$ of the first portion $402_A$, and the arms $404_{B1}$, $404_{B2}$, and $404_{B3}$ of the second portion $402_B$, may include a curvature matching that defined by the dissection element 300, as can be appreciated through reference to FIGS. 1 and 2.

To secure the restrictor 400 relative to the dissection element 300, the arms $404_{A1}$, $404_{B1}$ and the arms $404_{A2}$, $404_{B2}$ may be secured together through any suitable manufacturing procedure, including, but not limited to, welding using impulse, laser, or RF, or through the use of an adhesive. To further secure the restrictor 400 relative to the dissection element 300, one or more portions of the restrictor 400, e.g., one or more of the arms $404_{A1}$, $404_{A2}$, $404_{B1}$, $404_{B2}$, $404_{C1}$, $404_{C2}$, may also be secured to, or monolithically formed with, the material from which the dissection element 300 is formed, e.g., the layers $302_A$, $302_E$ (FIG. 4).

Figure 7:
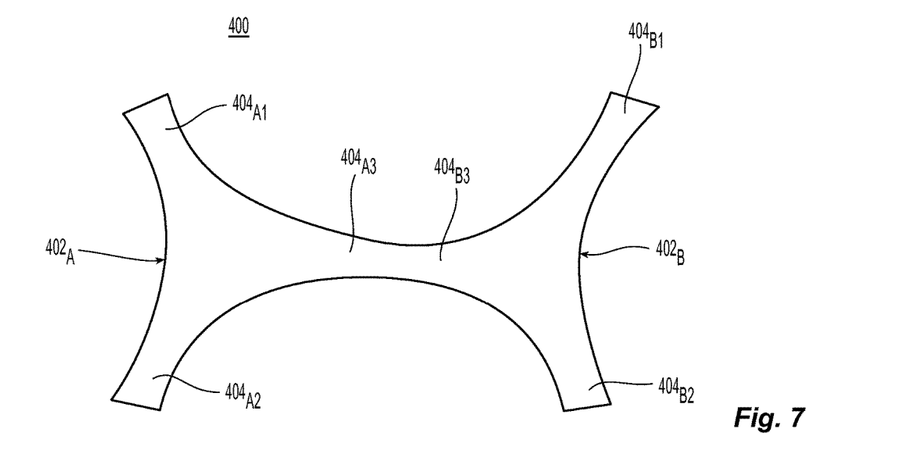
FIG. 7 is a plan view of the restrictor seen in FIGS. 1 and 2.

In one embodiment, such as that represented in FIG. 7, the restrictor 400 may be formed from a single piece of material in order to eliminate separation between the arms $404_{A3}$, $404_{B3}$ of the respective first and second portions $402_A$, $402_B$. In such embodiments, in positioning the restrictor 400 relative to the dissection element 300, the arms $404_{A3}$, $404_{B3}$ may be bent or deformed as required.

Figure 8:
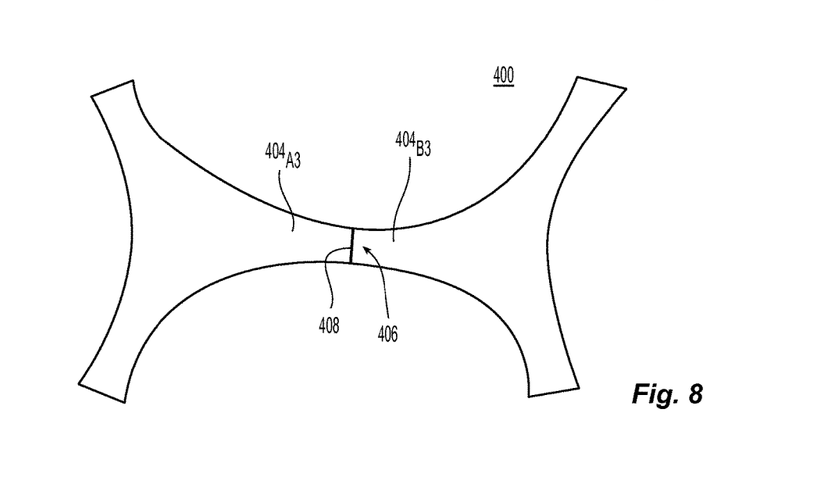
FIG. 8 is a plan view of an alternate embodiment of the restrictor seen in FIG. 7.

In another embodiment, such as that represented in FIG. 8, one or more of the arms, e.g., the arms $404_{A3}$, $404_{B3}$, may be connected to one another via a hinge element 406, e.g., a living hinge 408.

The restrictor 400 may include any number of arms, or be configured in any manner, which facilitates the intended purpose of restricting expansion of the dissection element 300 in one or more directions. The restrictor 400 may be positioned such that portions of the restrictor 400 are positioned adjacent portions of the dissection element 300 that are capable of greater expansion than other portions of the dissection element 300.

Figure 7A:
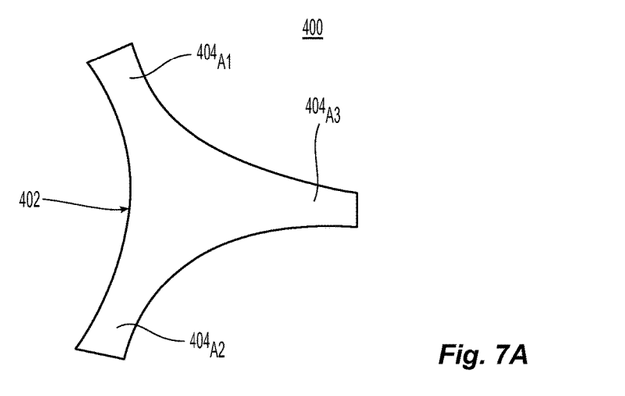
FIG. 7A is a plan view of an alternate embodiment of presently disclosed restrictor.

In another embodiment, which is illustrated in FIG. 7A, the restrictor 400 includes a single body portion 402 having a first arm $404_{A1}$, a second arm $404_{A2}$, and a third arm $404_{A3}$, and is configured and dimensioned for positioning adjacent one side of the dissection element 300 only, rather than adjacent opposing sides of the dissection element 300, e.g., as illustrated in FIG. 4, for example.

The restrictor 400 may be of varying rigidity or flexibility, for example, via the inclusion of various material(s) of construction, by varying the thicknesses of the materials of construction, and/or by varying the number of layers of material. For example, with reference to FIG. 2, the restrictor 400 may be of greater rigidity at the location wherein the arms $404_{A1}$, $404_{A2}$, $404_{A3}$ intersect relative to the rigidity of the arms $404_{A1}$, $404_{A2}$, $404_{A3}$ themselves. Alternatively, one or more of the arms $404_{A1}$, $404_{A2}$, $404_{A3}$ may be of different flexibility.

With reference now to FIGS. 1, 2, and 4, a method of performing a surgical procedure with the dissector assembly 1000 will be discussed. Initially, the dissector assembly 1000 is advanced through an opening O in the tissue T, which may be either naturally occurring or surgically created, such that the dissection element 300 is positioned internally, beneath the tissue T, in a desired location. Thereafter, fluid is communicated into the dissection element 300, e.g., through the cannula assembly 100, to move the dissection element 300 into the expanded condition seen in FIG. 1. During expansion of the dissection element 300, the adjacent tissue layers $T_1$, $T_2$ are separated in order to create the internal worksite W. As the dissection element 300 is expanded, an inwardly directed force F (FIG. 4) is applied to the dissection element 300 by the restrictor 400 in order to inhibit expansion of the dissection element in at least one direction. For example, in the particular embodiment illustrated in FIG. 4, the restrictor 400 inhibits expansion of the dissection element 300 along the Y axis, thereby limiting tissue displacement along the Y axis, such that the dissection element 300 defines the illustrated generally planar configuration in the expanded condition.

During expansion of the dissection element 300, an endoscope (not shown), or other suitable viewing instrument may be inserted into the dissection element 300, e.g., via the cannula assembly 100, in order to facilitate visualization of the tissue, e.g., the internal worksite W. As mentioned above, the dissection element 300 may include translucent portions, transparent portions, or combinations thereof, whereby the tissue, e.g., the internal worksite W, can be visualized directly through the dissection element 300.

Following creation of the internal worksite W, fluid can be withdrawn from the dissection element 300 so as to return to the dissection element 300 to the unexpanded condition, and the dissector assembly 1000 can be withdrawn from the patient.

Figure 9:
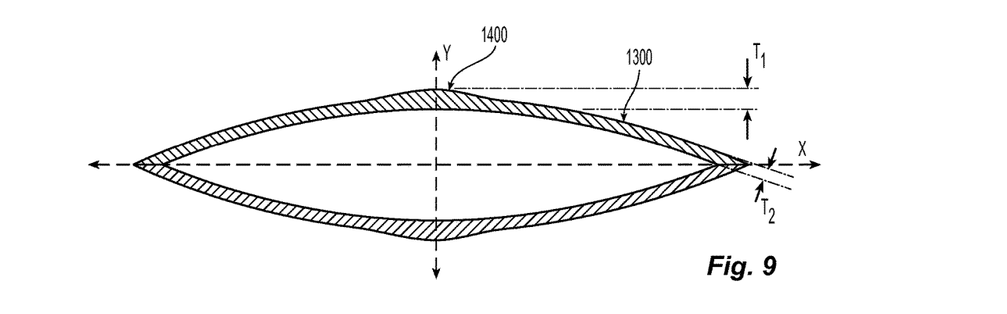
FIGS. 9-11 are cross-sectional illustrations of alternate embodiments of the presently disclosed dissection element and restrictor.
Figure 10:
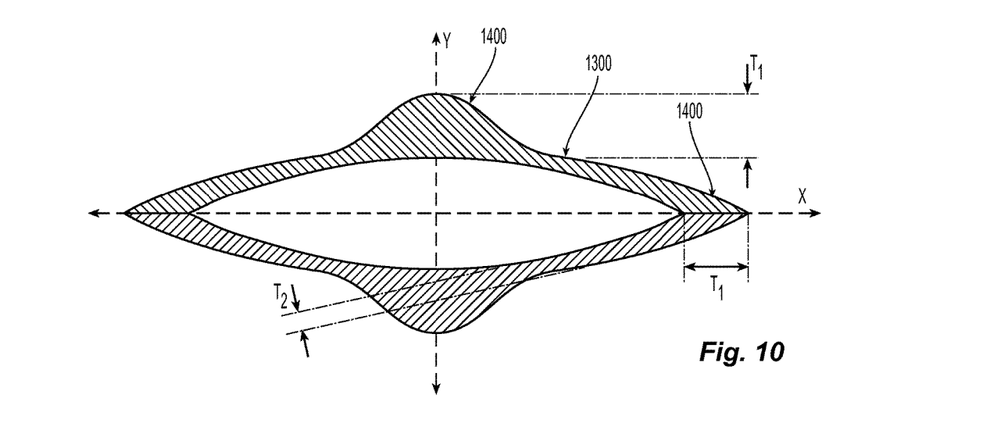
Figure 11:
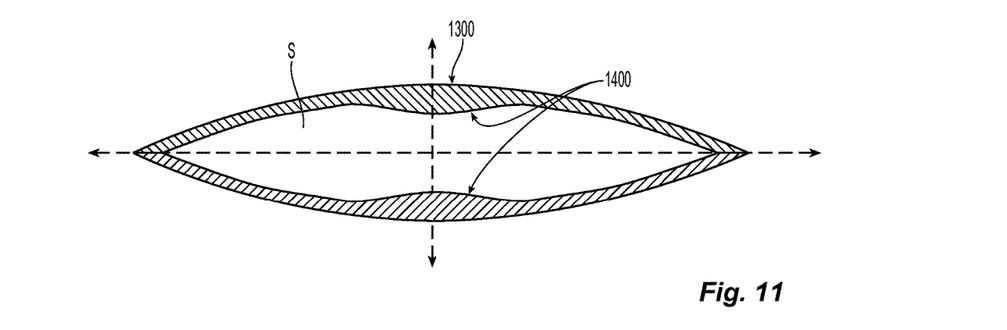

With reference now to FIGS. 9-11, alternate embodiments of the dissection element and the restrictor will be discussed, which are identified by the reference characters 1300 and 1400, respectively. The dissection element 1300 and the restrictor 1400 are identical to the dissection element 300 and the restrictor 400 discussed above with respect to FIGS. 1, 2, and 4, for example, but for the differences described below.

In the embodiments shown, the restrictor 1400 is integrally formed with the dissection element 1300, and is formed from the same material of construction as the dissection element 1300, e.g., clear urethane. In order to reduce the resiliency of the restrictor 1400 relative to the dissection element 1300, the restrictor 1400 defines an increased thickness, i.e., a larger cross-sectional dimension along the axis in which limited expansion of the dissection element 1300 is desired. For example, with reference to FIG. 9, the thickness $T_1$ of the restrictor 1400 is increased in relation to the thickness $T_2$ of the dissection element 1300 along the Y axis in order to limit expansion of the dissector element 1300 along the Y axis. Since it may be desirable to limit expansion of the dissector element 1300 in additional dimensions, in additional embodiments of the disclosure, the thickness $T_1$ of the restrictor 1400 may be increased in additional locations. For example, with reference to FIG. 10, the thickness $T_1$ of the restrictor 1400 may be increased in relation to the thickness $T_2$ of the dissection element 1300 to limit expansion of the dissector element 1300 along the X axis in addition to the Y axis.

It is envisioned that the restrictor 1400 may extend outwardly from the dissection element 300, as seen in FIGS. 9 and 10, for example. Alternatively, it is envisioned that the restrictor 1400 may extend inwardly into the interior space S defined within the dissection element 1300, as seen in FIG. 11, for example.

Figure 12:
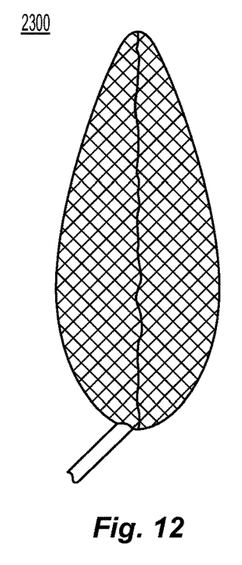
FIG. 12 is a rear view of an alternate embodiment of the presently disclosed dissection element.
Figure 13:
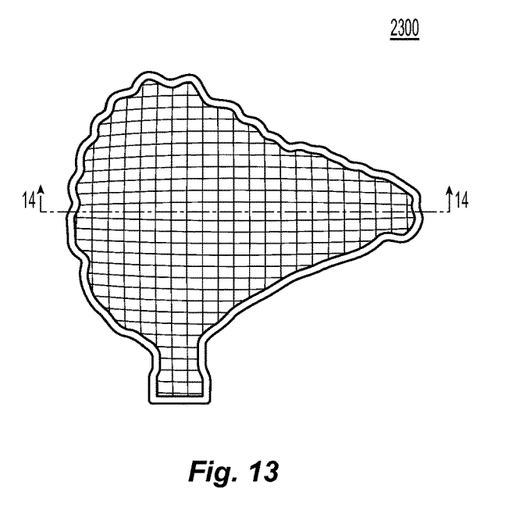
FIG. 13 is a top view of the embodiment of the dissection element seen in FIG. 12.
Figure 14:
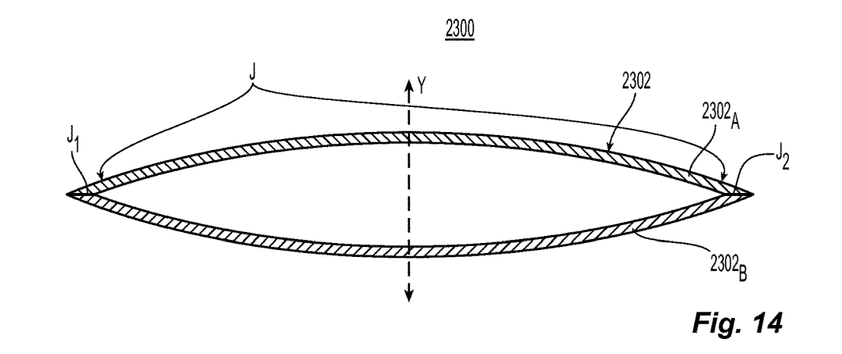
FIG. 14 is a cross-sectional illustration of the dissection element seen in FIG. 13 along line 14-14.

With reference now to FIGS. 12-14, another embodiment of the dissection element will be discussed, which is identified by the reference character 2300. The dissection element 2300 is identical to the dissection element 300 discussed above with respect to FIGS. 1, 2, and 4, for example, but for the differences described below.

The dissection element 2300 is formed from one or more materials of construction that inherently restrict expansion of the dissection element 2300 in one or more directions beyond a certain predetermined measure. For example, the materials of construction may restrict expansion of the dissection element 2300 beyond a particular volume, or may restrict expansion of the dissection element 2300 such that the expansion element 2300 defines a particular configuration in the expanded condition.

The particular materials of construction for the dissection element 2300 obviate the need for a separate, discrete restrictor element, and thus, reduce the cost and complexity of manufacture. For example, in one embodiment, the dissection element 2300 may be formed entirely from ripstop nylon, or from one or more layers of film having a high modulus of elasticity, e.g., high durometer polyurethane, polyethylene, mylar, or other suitable laminates. Alternatively, the dissection element 2300 may include one or more layers of a first material, e.g., a urethane film, that are reinforced with one or more layers, strips, ribs, or other such portions of a second material, e.g., ripstop nylon or flash-spun high-density polyethylene fibers.

With reference to FIG. 14 in particular, in the illustrated embodiment, the dissection element 2300 is formed from layers 2302 of material, e.g., layers $2302_A$, $2302_B$, that are secured together at one or more junction points J, e.g., junction points $J_1$, $J_2$, through any suitable manufacturing procedure, including, but not limited to, welding using impulse, laser, or RF, or through the use of an adhesive. The dissection element 2300 is configured and formed to restrict expansion in a direction perpendicular to the junction points $J_1$, $J_2$, i.e., along the Y axis in the illustrated embodiment.

Although illustrated as being formed from multiple layers 2302 of material that are secured together at multiple junction points, i.e., the aforedescribed junction points $J_1$, $J_2$, it should be appreciated that the dissection element 2300 may also be formed from a single layer 2302 of material secured to itself at single junction point, or at a plurality of junction points. For example, a single layer 2302 of material may be folded onto itself.

Figure 15:
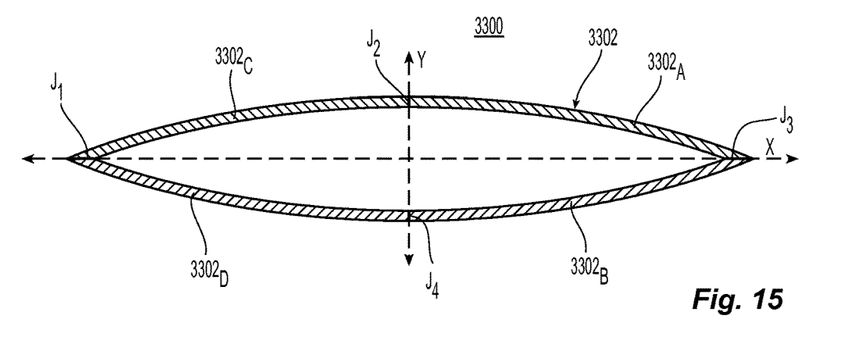
FIG. 15 is a cross-sectional illustration of another embodiment of the presently disclosed dissection element.

FIG. 15 illustrates another embodiment of the dissection element, which is identified by the reference character 3300. The dissection element 3300 is identical to the dissection element 2300 discussed above with respect to FIGS. 12-14, but for the differences described below.

The dissection element 3300 includes layers 3302 of material, e.g., layers $3302_A$, $3302_B$, $3302_C$, $3302_D$, that are secured together at junction points $J_1$, $J_2$, $J_3$, $J_4$. As discussed in connection with the dissection element 2300 illustrated in FIG. 14, the dissection element 3300 is configured and formed to restrict expansion in directions perpendicular to the junction points $J_1$, $J_2$, $J_3$, $J_4$. As such, in the embodiment illustrated in FIG. 15, the layers 3302 of material restrict expansion of the dissection element 3300 in multiple dimensions, i.e., along the X and Y axes.

Persons skilled in the art will understand that the various apparatus, and corresponding methods of use described herein and shown in the accompanying drawings, constitute non-limiting, exemplary embodiments of the present disclosure, and that additional components and features may be added to any of the embodiments discussed herein above without departing from the scope of the present disclosure. For example, the various embodiments of the dissector assemblies described herein may be modified to include a pressure sensor in order to monitor pressure within the various dissection elements, and/or an escape valve in order to inhibit over expansion.

Additionally, persons skilled in the art will understand that the elements and features shown or described in connection with one exemplary embodiment may be combined with those of another exemplary embodiment without departing from the scope of the present disclosure, and will appreciate further features and advantages of the presently disclosed subject matter based on the above-described embodiments and the claims. Accordingly, the present disclosure is not limited by what has been particularly shown and described.

What is claimed is:

1. A surgical apparatus configured and dimensioned to create an internal surgical worksite, the surgical apparatus comprising: an expandable dissection element having a first resiliency and being expandable to an expanded configuration; and a restrictor formed of a single piece of material having a second resiliency less than the first resiliency, the restrictor being fixedly secured to the dissection element, the restrictor including a pair of first arms and a pair of second arms, the pair of first arms being secured together with a hinge element, wherein the hinge element is a living hinge, and the pair of second arms being secured together, the restrictor being configured to restrict expansion of the dissection element in at least one direction such that the dissection element defines a generally planar configuration in the expanded configuration.

2. The surgical apparatus of claim 1, wherein the dissection element is formed from a first material and the restrictor is formed from a second material different than the first material.

3. The surgical apparatus of claim 2, wherein the first material has a first durometer, and the second material has a second, greater durometer.

4. The surgical apparatus of claim 3, wherein the dissection element is formed from urethane, and the restrictor is formed from nylon.

5. The surgical apparatus of claim 1, wherein the dissection element and the restrictor are configured as discrete structures.

6. The surgical apparatus of claim 5, wherein the restrictor is positioned externally of the dissection element.

7. The surgical apparatus of claim 5, wherein the restrictor is positioned internally within the dissection element.

8. The surgical apparatus of claim 5, wherein the restrictor is positioned between adjacent layers of the first material.

9. The surgical apparatus of claim 1, wherein the pair of first arms are welded together, and the pair of second arms are welded together.

10. The surgical apparatus of claim 1, wherein the dissection element and the restrictor are formed from the same material.

11. The surgical apparatus of claim 10, wherein the dissection element and the restrictor are monolithically formed with one another.

12. The surgical apparatus of claim 11, wherein the dissection element defines a first thickness, and the restrictor element defines a second, greater thickness.

13. The surgical apparatus of claim 1, wherein the dissection element is at least partially formed from a material permitting at least some light to pass therethrough.

14. A surgical apparatus configured and dimensioned to create an internal surgical worksite, the surgical apparatus comprising:
   an expandable dissection element having a first resiliency and being expandable to an expanded configuration; and
   a restrictor having a second resiliency less than the first resiliency, the restrictor being fixedly secured to the dissection element, the restrictor including a pair of first arms and a pair of second arms, the pair of first arms being secured together with a living hinge, and the pair of second arms being secured together, the restrictor being configured to restrict expansion of the dissection element in at least one direction to control the expanded configuration of the expandable dissection element.

15. A surgical apparatus configured and dimensioned to create an internal surgical worksite, the surgical apparatus comprising:
   an expandable dissection element having a first resiliency and being expandable to an expanded configuration; and
   a restrictor having a second resiliency less than the first resiliency, the restrictor being monolithically formed with the dissection element, the restrictor including a pair of first arms and a pair of second arms, the pair of first arms being secured together by a living hinge, and the pair of second arms being secured together, the restrictor being configured to restrict expansion of the dissection element in at least one direction such that the dissection element defines a generally planar configuration in the expanded configuration of the expandable dissection element.

* * * * *

UNITED STATES PATENT AND TRADEMARK OFFICE
CERTIFICATE OF CORRECTION

PATENT NO. : 10,166,376 B2
APPLICATION NO. : 14/247286
DATED : January 1, 2019
INVENTOR(S) : Okoniewski et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 294 days.

Signed and Sealed this
Thirtieth Day of July, 2019

Andrei Iancu
*Director of the United States Patent and Trademark Office*